(12) United States Patent
Darby et al.

(10) Patent No.: US 7,163,513 B2
(45) Date of Patent: Jan. 16, 2007

(54) PSYCHOLOGICAL TESTING METHOD AND APPARATUS

(75) Inventors: David Darby, Melbourne (AU); Ashley Bush, Somerville, MA (US)

(73) Assignee: Cogstate, Ltd., Victoria (AU)

( * ) Notice: Subject to any disclaimer, the term of this patent is extended or adjusted under 35 U.S.C. 154(b) by 229 days.

(21) Appl. No.: 10/343,067

(22) PCT Filed: Jul. 27, 2001

(86) PCT No.: PCT/AU01/00924

§ 371 (c)(1),
(2), (4) Date: Jul. 31, 2003

(87) PCT Pub. No.: WO02/11102

PCT Pub. Date: Feb. 7, 2002

(65) Prior Publication Data

US 2005/0192513 A1    Sep. 1, 2005

(51) Int. Cl.
*A61B 13/00* (2006.01)

(52) U.S. Cl. .................................................. 600/558

(58) Field of Classification Search ................. 600/558, 600/300; 434/236, 156; 351/223, 239, 224, 351/246
See application file for complete search history.

(56) References Cited

U.S. PATENT DOCUMENTS

| | | | |
|---|---|---|---|
| 5,801,810 A * | 9/1998 | Roenker | 351/246 |
| 6,030,226 A * | 2/2000 | Hersh | 434/236 |
| 6,045,515 A * | 4/2000 | Lawton | 600/558 |
| 6,113,538 A * | 9/2000 | Bowles et al. | 600/300 |
| 2003/0059750 A1 * | 3/2003 | Bindler et al. | 434/236 |

* cited by examiner

*Primary Examiner*—Max F. Hindenburg
*Assistant Examiner*—Brian Szmal
(74) *Attorney, Agent, or Firm*—Duane Morris LLP

(57) ABSTRACT

A method for psychological testing of a subject is performed by (A) presenting a test by means of a testing means having output means (e.g. a computer monitor) and input means (e.g. a keyboard); and, (B) instructing the subject by displaying a simulation (as shown in the figure) of the test by means of the output means so that the subject can learn how to perform the test from the simulation. The test is therefore independent of the subject's language skills, or of verbal instructions provided by a supervisor.

38 Claims, 10 Drawing Sheets

PSYCHOLOGICAL TESTING METHOD AND APPARATUS

This application is the National Phase of International Application PCT/AU01/00924 filed 27 Jul. 2001 which designated the U.S. and that International Application was published under PCT Article 21(2) in English.

FIELD OF THE INVENTION

The present invention relates to a method and apparatus for psychological testing, of particular but by no means exclusive application in the on-line testing of remote test subjects.

BACKGROUND OF THE INVENTION

Existing psychological testing techniques include memory tests, fluid intelligence tests, intelligence quotient tests and chronometric based tests. Some said tests are available on-line at web sites.

However, existing techniques have a number of shortcomings. These include the fact that verbal instructions must be used in demonstrating the test to a test subject, such verbal instructions being presented to the subject in printed or oral form. The subjects must then translate the words into a state-dependent set of expectations about the type of stimulus-response requirements that will be encountered in the test. The translation process, however, is dependent upon the individual subject's language skills in the language of the instructions, and that subject's experience in using language to govern his or her behaviour.

Further, instructions provided in this manner, either by the interpretation of written instructions or by the verbal instruction provided by a supervisor conducting the test (as well as subsequent interactions between that supervisor and the test subject), can lead, almost inevitably, to the inadvertent altering of the test environment. This effect may be due to variations in the level of understanding by the subject, or instruction or subsequent interaction provided by the supervisor, who may conclude that more or less instruction, for example, is required for a particular subject. In some contexts this flexibility may be of value, but small changes in the test conditions can mask poor performance or, alternatively, can impair normal performance.

Other existing techniques are culturally dependent: at the simplest level, the use of verbal or written instructions as discussed above can impact on testing, because different instructions must be provided according to the language of the subject, thereby introducing variation dependent on the skill exercised in translating the instructions, and because some languages may be better adapted than others to expressing the necessary instructions. Most existing techniques employ tests that have a small number of forms, so that subjects repeating the test may soon re-encounter a test, or may deduce the nature of the variation between tests and benefit accordingly.

It is an object of the present invention to provide a psychological testing method and apparatus that avoids one or more of the above shortcomings.

SUMMARY OF THE INVENTION

The present invention provides, therefore, a psychological testing method for testing a subject, including:
performing said method by means of a test presented by means of a testing means having output means and input means; and
instructing said subject by displaying a test simulation of said test by means of said output means;
whereby said subject can learn how to perform said test from said simulation.

Thus, the test subject may, but is not required, to read or listen to instructions, or be instructed by a test supervisor in order to learn how to perform the test.

Furthermore, in order actually to conduct the test, once learned, the test subject will preferably perform the test without written instructions or instruction from a test supervisor.

Preferably, said method includes repeating said simulation a plurality of times.

Preferably, said method is performed by means of a plurality of tests, and instructing said subject includes displaying a test simulation of each of said plurality of tests, whereby said subject can learn how to perform each of said tests.

Preferably, said method includes said subject performing said test by using said input means after said subject is instructed.

Preferably, where said method is performed by a plurality of tests, said method includes alternating between said subject being instructed and said subject performing a test.

Thus, the subject is instructed as to how to perform each test immediately before performing that test.

Preferably, said method includes terminating said instructing of said subject and commencing assessing said subject when said subject is able to satisfy a criterion of comprehension of the test. For example, the criterion may be successful performance of three consecutive trial tests.

Thus, when the subject provides a response to a simulated test before the simulation itself displays the appropriate response, the method ceases instructing the subject and begins assessing the subject.

Preferably, said output means is a display means, and more preferably a computer monitor, and the input means is a computer keyboard and/or mouse However, the output means may be an audio output, or may be a combination of outputs.

Preferably, said test of said method includes displaying visual stimuli.

Preferably, said test of said method includes randomly varying a time at which said visual stimuli is displayed.

Preferably, said method includes measuring the response time of said subject.

Preferably, said method includes disregarding a response with less than a predetermined minimum response time.

Thus, if a subject anticipates the response, he or she may provide a response faster than is physically or psychologically possible (i.e. below a base level reaction time), so that response should preferably be disregarded.

Preferably, the method includes presenting substantially a cultural stimuli to said subject. More preferably said stimuli comprise representations of playing cards, dominoes, playing counters, or similar widely recognised game playing indicia.

Preferably, displaying said test simulation includes displaying the correct use of said input means to perform said test.

The invention also provides psychological testing apparatus for testing a subject, said apparatus including testing means having output means and input means, said testing means testing said subject by presenting a test to said subject, said apparatus instructing said subject by displaying a test simulation of said test on said output means, whereby said subject can learn how to perform said test by means of said apparatus from said simulation.

Preferably, said testing means is a computer programmed to present said test to said subject. It will be understood that the term "computer" can encompass any appropriate computing device or combination of computing devices, for example, a stand-alone computer or the combination of a host computer and a client computer.

Preferably, said output means is a display means and more preferably a computer monitor and said input means is a keyboard.

The invention also provides a method of monitoring the performance of a subject using the above psychological testing method, including obtaining a reference test result by a subject performing the testing method repeatedly until said subject is satisfied that they have performed said testing method at a near optimum level and using the result of the test performed at a near-optimum level as a reference test result;

obtaining a comparison test result by a subject performing said testing method repeatedly at a time at which the subject's performance is to be monitored until said subject is satisfied that they have performed the testing method at a near optimum level, and using the result of the test performed at a near optimum level as a comparison test result; and comparing said comparison test result with said reference test result to thereby monitor the performance of the subject.

Thus, any deterioration in the subject's performance can be noted.

Preferably, said method includes obtaining a number of comparison test results and using said comparison test results to monitor said subject's performance.

The invention also provides apparatus for monitoring the performance of a subject using the above psychological testing apparatus, wherein said apparatus obtains a reference test result by allowing a subject to perform the test repeatedly until said subject provides an input via said input means which indicates that the subject is satisfied that he/she has performed said testing method at a near optimum level, wherein said apparatus includes a storage means for storing said result of the test performed at a near optimum level as a reference test result for said subject;

said apparatus obtaining a comparison test result by allowing a subject to perform said test repeatedly at a time at which the subject's performance is to be monitored until said subject provides an input via said input means which indicates that said subject is satisfied that they have performed the testing method at a near optimum level, said apparatus retrieving the stored reference test result and comparing said comparison test result with said reference test result to thereby monitor the performance of the subject.

The present invention further provides a psychological testing method for testing a subject, including:

performing said method by means of a plurality of tests presented by means of a testing means having output means and input means;

measuring for each of said tests a response time of said subject; and determining changes in said response times over the duration of said tests.

Preferably, said method includes disregarding any of said response times with less than a predetermined minim response time.

The present invention further provides psychological testing apparatus for testing a subject, including:

a testing means having output means and input means, said testing means testing said subject by presenting a plurality of tests to said subject;

said testing means measuring for each of said tests a response time of said subject; and said testing means determining changes in said response times over the duration of said tests.

Preferably, said testing means disregards any of said response times with less than a predetermined minimum response time.

The method and apparatus of the invention are suitable for administering a variety of psychological tests, including but not limited to tests of cognitive ability, memory function, decision-making function, concentration function, and problem-solving function. These tests are useful for assessing cognitive ability and/or its impairment by factors such as fatigue, alcohol intake, intake of drugs of abuse or therapeutic drugs, or underlying medical conditions which affect cognition. The method and apparatus of the invention are thus useful in assessing suitability of personnel to perform demanding tests, eg military personnel, airline pilots, sportspersons, or transport drivers. It will be appreciated that the test can also be used in a clinical setting, for example to measure a decline in performance resulting from progression of a clinical condition, or an improvement in such a condition resulting from therapeutic intervention (eg drug treatment).

BRIEF DESCRIPTION OF THE DRAWINGS

In order that the present invention may be more clearly ascertained, a preferred embodiment will now be described, by way of example, with reference to the accompanying drawings, in which.

DESCRIPTION OF THE PREFERRED EMBODIMENT

In the preferred embodiment, psychological testing apparatus for carrying out a psychological testing method for testing a subject is provided in the form of a computer program loaded onto a personal computer, whereby the personal computer (PC) provides output means, in the form of a computer monitor, and input means in the form of a keyboard and/or mouse—the personal computer is loaded with software thus providing a testing means. The computer program can be preloaded on the PC or downloaded from the Internet, for example, in the form of a Java applet. It will be appreciated that the software resident on the PC may only be part of the software. For carrying out the software method. For example, the psychological testing may be carried out over the Internet, in which case a likely configuration is that a part of the software will run on the host computer and a part of the software will be resident on the PC or client computer, with data generated by the software running on the client computer being automatically transmitted to the host computer. Thus, results generated by the testing apparatus can be stored in a memory associated with the host computer at a site remote from where the test is carried out.

Once a series of introductory steps have been completed, such as the launching of the software and a series of registration steps have been completed, the psychological testing method begins. The method operates essentially by instructing the subject by displaying a test simulation of each test on the computer monitor whereby the subject can learn how to perform the test from the simulation.

The test simulation includes displaying on the computer monitor the correct use of the keyboard, which is the preferred input means, to perform the test. Thus, from observing the simulation, the subject can learn how to use the keyboard to perform the test correctly. While the test subject is not required to read or listen to instructions or to be instructed by a test supervisor in order to perform the tests, it will be clearly understood that verbal or written instructions may optionally be provided, even though reference to such instructions need no be made in order to understand how to perform the test as this can be learnt from the simulation.

An example of how the testing method could be performed is now given in order to facilitate understanding of the broad inventive concept, as well as a number of other inventive features of the psychological testing method and apparatus.

Figure 1:
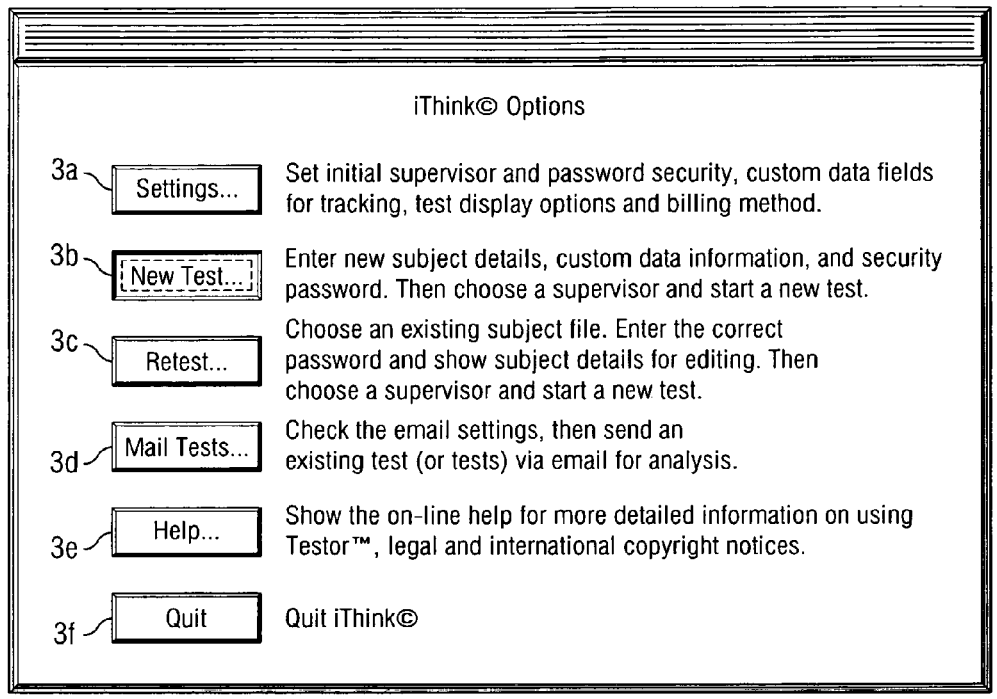
FIG. 1 shows a logon screen of the invention.

The subject to be tested sits at a comfortable viewing distance in front of a personal computer loaded with the computer program. Each PC can only test one subject at a time. A test usually lasts about 15–20 minutes. The program is initiated, eg by double clicking the associated application icon, and the monitor displays. A dialog box (2) as shown in FIG. 1 with buttons 3 displaying the available options.

These include options to start a new test ("New Test . . . ") 3a, retest a subject already tested at least once before ("Retest . . . ") 3b, view the on-line help information ("Help . . . ") 3c, e-mail previous completed test results for analysis ("Mail Tests . . . ") 3d, adjust the program's settings ("Settings . . . ") 3e, or leave iThink immediately ("Quit") 3f. If this dialog box 2 is dismissed by selecting one of the options, these items have menu equivalents which can be selected to perform similar actions without the need for the dialog box 2. The provision of appropriate equivalent menu items as well as the dialog is within the skills of a computer programmer and hence not described in further detail.

Usually, a subject will click either the "New Test . . . " button 3b (or the equivalent menu item) to begin a new test, or the "Retest . . . " button 3c if they have prior test data or formerly cancelled a test without completing it. If they wish to view the on-line help or adjust test settings they can click the respective buttons (and can then choose the equivalent menu items to initiate or continue testing ie. "New Subject . . . " for "New Test . . . ", "Open Subject . . . " for "Retest . . . ").

Figure 2:
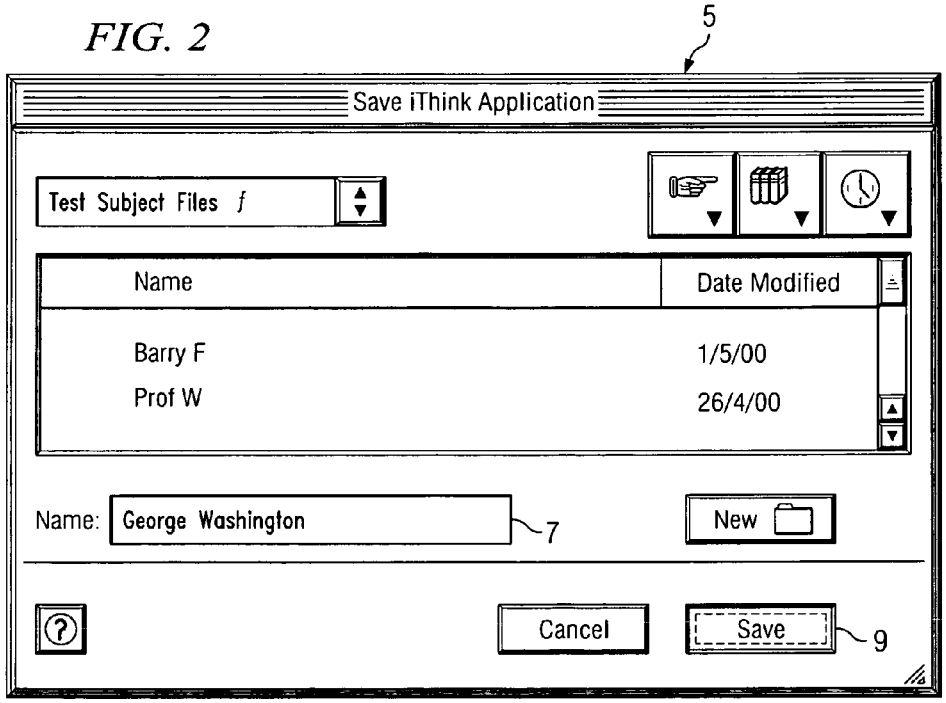
FIG. 2 shows a screen used to create a new user entry.

Once a subject initiates a new test, they must first create a subject file into which their details and test data will be saved at the completion of the test. They will be presented with a standard save file dialog box 5 as shown in FIG. 2. The subject can navigate to a folder of their choice (usually determined by the supervisor) or use the default setting (where a file was saved last time). The subject needs to type in their name or some other file name identifier 7 and then click the Save button 9 to save this file.

Figure 3:
FIG. 3 shows a screen used to enter subject details.
Figure 4:
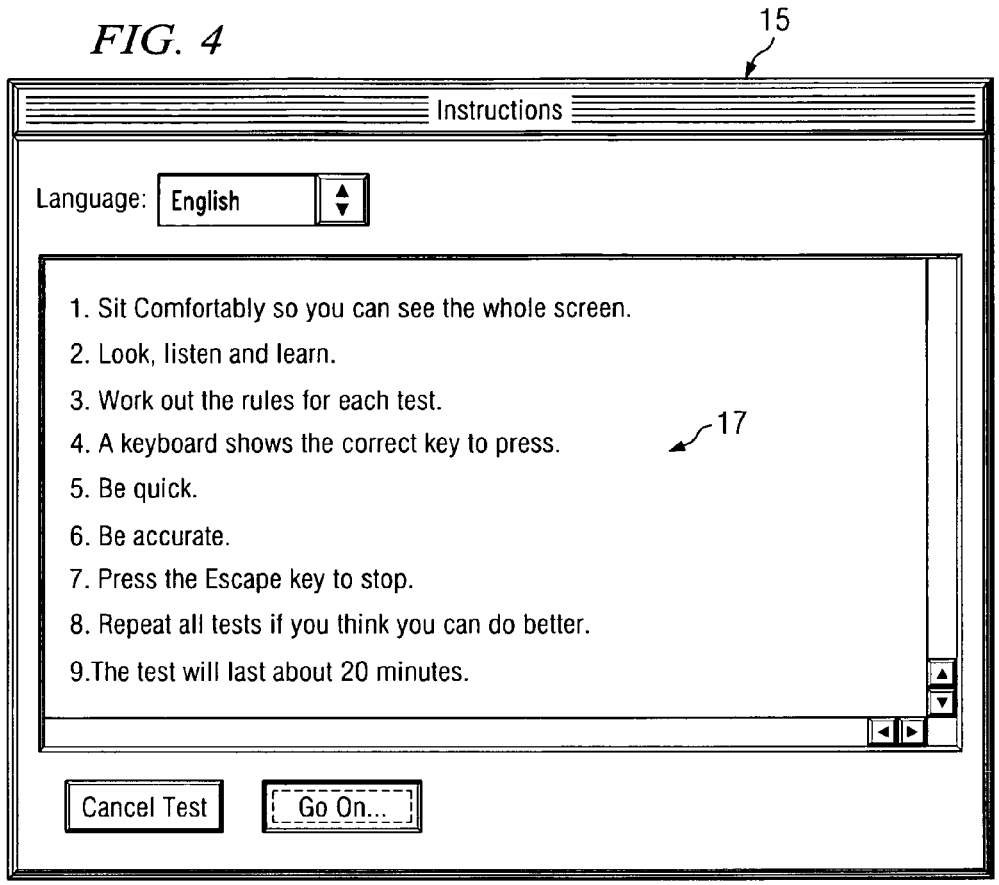
FIG. 4 shows initial instructions to be provided to the subject.

They are next presented with a subject details dialog box 10 (FIG. 3) with editable fields 11 requesting personal information such as: prefix 11a, first name 11b, last name 11c, title 11d, company 11e, a first address line 11f, a second address line 11g, city 11h, state 11i, zip code 11j, country 11k, phone 11l, fax 11m, e-mail address 11n, birth year 11o. If desired, a code name or number or minimum identification details may alternatively be used. Certain fields are mandatory and must be completed to continue. In addition there are a number of pop-up menus for details which have a limited number of responses and which may affect the conducting of the testing method or the results of the testing method or be useful for analysis of results of a number of testing methods. These menus include gender menu 13a with possible selections of male or female; handedness menu 13b with selections of right—2 hands, left—2 hands, ambidextrous, right—1 hand, and left—1 hand; and a education 13c with selection of primary, secondary or tertiary.

When the subject's details have been entered, the subject is required to set a password which must be entered in order to verify that the subject is performing the test.

Test data is recorded in a log window which is invisible to the subject using text codes and times. Appropriate test data recording techniques will be apparent to those skilled in the art and further details are not provided herein.

Once the initial registration steps have been carried out, an introductory screen of instructions including a plurality of instructions 17 may be displayed in order to provide some indication as to how to respond to the overall testing method, without explaining how individual tests of the testing method should be performed. This explanation being left to simulation of the tests. This screen 15 need not be displayed in all embodiments.

Each test of the testing method can include two distinct phases: a simulation phase in which the test is shown to the subject and a testing stage when the subject performs the test in accordance with the rules learnt during the simulation stage.

Figure 5:
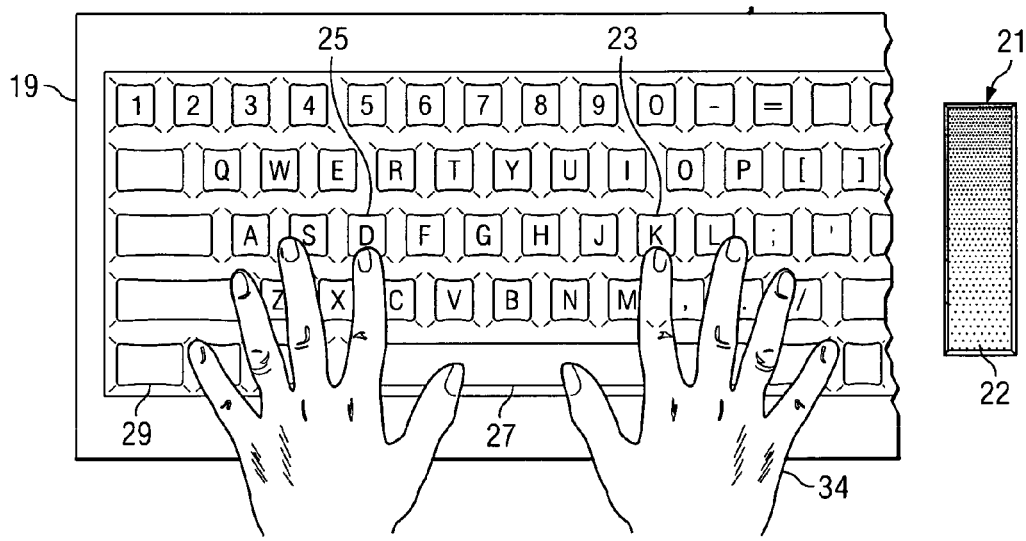
FIG. 5 shows a keyboard simulation and a response meter.

Each test is based on the display of virtual playing cards as visual stimuli. Playing cards are chosen as they are generally a cultural and also contain a number of levels of information. The tests involve different presentation of the playing cards on the display to the user in order to measure different aspects of cognition. when a test is simulated a keyboard is represented on the display with overlying hands as shown in FIG. 5. In some of the tests a response meter 21 is provided to give the user feedback as to their speed of response to part of the test or demonstration. In each test, the simulation phase includes displaying cards in a particular manner and indicating by highlighting a relevant section of the display of the keyboard how the user should respond to the test. The response meter provides a further indication as to whether the user is responding sufficiently rapidly. Specifically, the response meter includes a coloured graphic bar which moves as time passes to give an indication of the time passed and the urgency of responding.

In general, in all tests, one or more packs of face-down cards will appear centrally on the display of the computer monitor. At some random time cards will turn face-up on top of the pack or beside the pack. Each card will require a specific response by the subject—i.e. by pressing one key of the keyboard. Depending on the handedness selection made in the subject details dialog box 10, different keys will be designated as "true" or "false" and the keys are chosen to ensure that the dominant hand is used to answer the "true"

condition. The correct key is determined by the rules of the test. In most tests there are only two keys to choose from. In some tests there is only one key and in some tests there are three keys to choose from. Typically, if the user is right handed then the "true" key will be on the right hand side of the keyboard.

More complicated tests may be devised which require the pressing of a larger number of keys if this is appropriate to the tests concerned.

In each test, the keyboard representation 19 will appear during the demonstration but will also reappear after a run of consecutive incorrect responses. Each test consists of a plurality of trials—i.e. a repetition of the test and the reaction time for each trial is recorded from 100 ms after the appearance of the face-up card(s) until a keyboard response is received.

Visual feedback is given to the subject which varies depending upon whether the response was correct or incorrect with cards returning to their deck in a different way, for a correct response and an incorrect response. An incorrect response may also illicit a sound. By providing visual feedback, the testing method provides the subject with an opportunity to learn as they go and correct their responses to various tests.

A number of tests are then performed.

1. Keyboard Key Test

Aim: To train the subject in response accuracy and speed using the keyboard.

The keyboard 19 and response meter appear 21 with 3 keys outlined in red. In FIG. 5, for a right handed subject these keys are the true 25, false 25 and space bar 27 keys, however any are easily used in combination. These keys initially flash sequentially twice to attract attention to them and then the hands (30, 29) appear from below and slide into the correct hand position. Specific keys then highlight in a randomized order. The subject is expected to press the highlighted key (23, 25, 27) as quickly as possible. The keys highlight every 1500–1700 ms. The response meter's internal coloured graphic 22 rises at a steady rate until the subject responds in order to provide an indication that the user should respond. It then stops so that they can inspect the colour achieved as a measure of their speed of response, and the key highlight disappears. For incorrect key presses, an error buzzer also sounds. No cards appear in this test and the keyboard remains throughout the subtest.

The test continues until each key has been pressed 3 times each, or at least once each and a total of 9 keys have been correctly pressed, or time runs out (60 seconds). Anticipatory and post-stimulus feedback errors (key responses) are also recorded.

Figure 6:
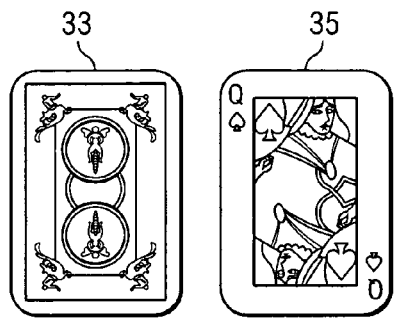
FIG. 6 shows a simple reaction test.

Trial Settings:
  Total required successes=9
  Stimulus Start=1500 ms
  Stimulus Stop time=0 ms
  Feedback duration=200 ms
  Post-ISI random range=0–200 ms
  Minimum reaction time start=1600 ms
  Maximum time for trial=5000 ms 2. Simple Reaction Test—See FIG. 6.

Aim: to test simple reaction time as a baseline for other cognitive reaction time tests.

Simulation Phase: A simulation first shows what the subject is expected to do. They initially see the keyboard (without hands) with the space bar key outlined in red, a central pack of cards face-down and the response meter. At random intervals between 1500–2500 ms a card appears face-up and the space bar key highlights (with an additional key pressing sound or click). A yellow shadowed arrow appears from the base of the face-up card to the space bar key pointing to it to indicate it should be pressed as soon as the card turns face-up. This repeats for a total of 3 times before the demonstration ends and the test trials begin. The subject can abort the simulation by the escape key or other cancel sequence.

Testing Phase: The test proper is exactly the same format though the subject must respond and no arrows appear. The sliding appearance of the hand(s) from the bottom of the screen indicates they should prepare to start responding. In addition, the card pack, keyboard & response meter disappear briefly and redraw. A single pack of face-down cards 33 then appears centrally (FIG. 6) concomitantly with a shuffling sound. After a variable period, between 1500–2500 ms, a face-up card 35 (randomly selected) appears on top of the central deck. At the same time, the space bar key 27 highlights. These remain as they are until a key is pressed. A reaction time is then recorded, and visual feedback commences (the space bar key unhighlights and, if they correctly pressed the space bar key, the card moves to the right turning over to face-down and slides underneath the deck or, if an incorrect key was pressed, turns to the left initially and an error buzzer sounds). This repeats with an inter-stimulus interval (ISI) varying between 1500–2500 ms showing the same card initially. If the trial takes longer than 5000 ms then the error feedback occurs whether or not the subject responds. The keyboard disappears after 3 correct consecutive trials and will reappear after 3 incorrect consecutive responses. The test ends when 12 correct responses have occurred to this same card and a further 3 correct responses to subsequent randomly presented cards, or a total test time of 60 seconds. Hence, after 12 correct responses, the cards displayed begin to randomly change to ensure they are aware of the importance solely of responding when the card turns face-up, not the card number & suit.

This simple reaction time test is repeated 2 other times throughout the whole test (after the combined monitoring task and at the very end after the associate learning task) in order to determine whether the subject is fatiguing or concentrating more poorly as the test goes on.

Trial Settings:
  Total required successes=12 (+3 extras*)
  Stimulus Start=1500 ms
  Stimulus Stop time=0 ms
  Feedback duration=200 ms
  Post-ISI random range=0–1000 ms
  Minimum reaction time start=1600 ms
  Maximum time for trial=5000 ms 3. Choice Reaction Test Aim: To assess a subject's efficiency in a simple choice reaction task, here choosing between red and black alternatives. Adding this simple choice component should increase reaction time by 50–150 ms approximately.

Simulation Phase: A simulation first shows what the subject is expected to do. The subject initially sees the keyboard (without hands) with the true and false keys outlined in red, and a central pack of cards face-down. Hence, this appearance is very similar to the simple reaction time task just completed. At random intervals between 1500–2500 ms a card appears face-up and the correct response key highlights accompanied by an additional key pressing sound or click. A yellow shadowed arrow appears from the base of the face-up card to the correct key pointing to it to indicate it should be pressed as soon as this type of card turns face-up. The cards in the simulation are not proper cards, but contain red or black colour filled rectangles. These are randomized in order of presentation during the simulation but continue until at least two of each have been presented and then the test proper begins.

Figure 10A:
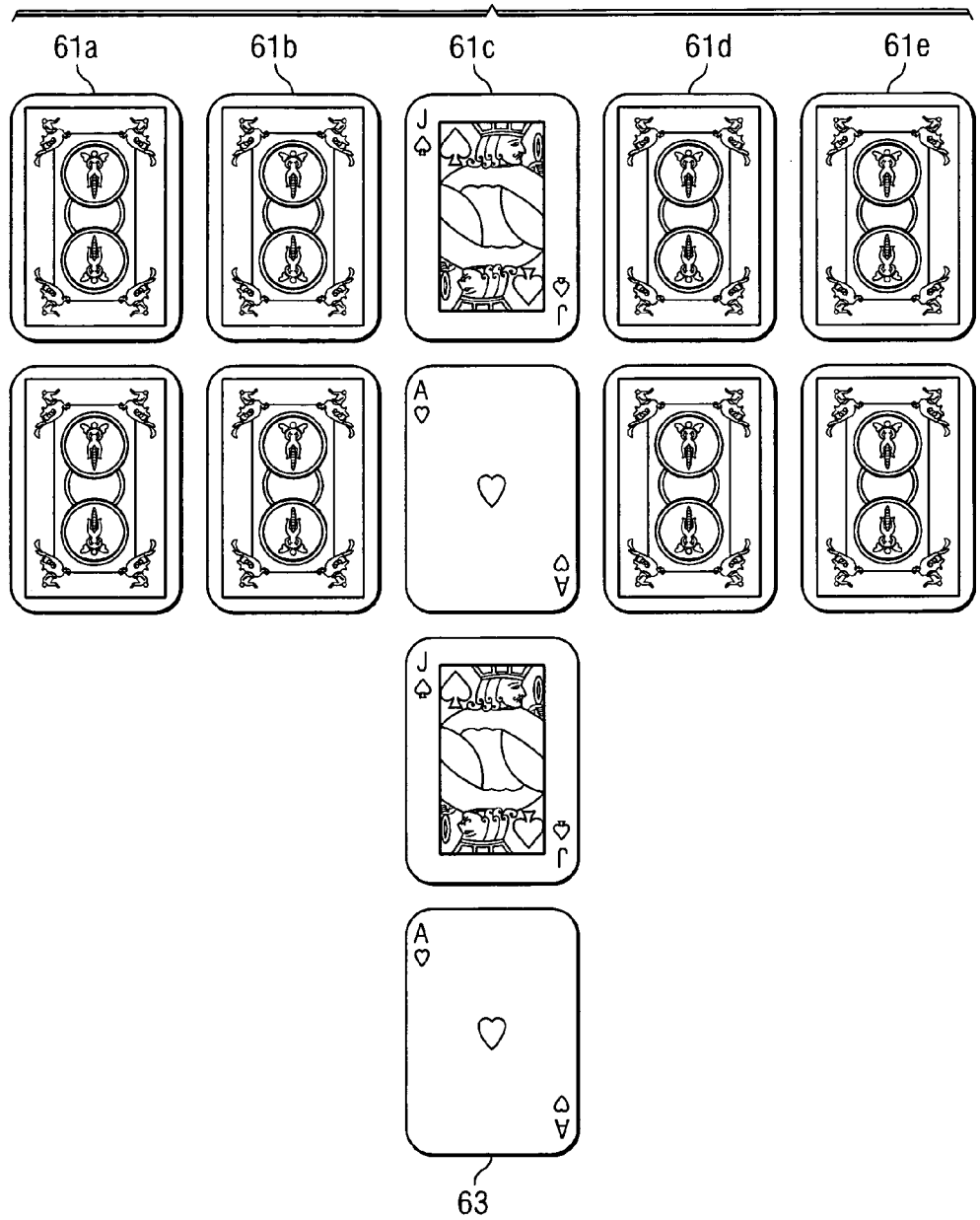
FIGS. 10A and 10B show cards used in an associated learning test.
Figure 10B:
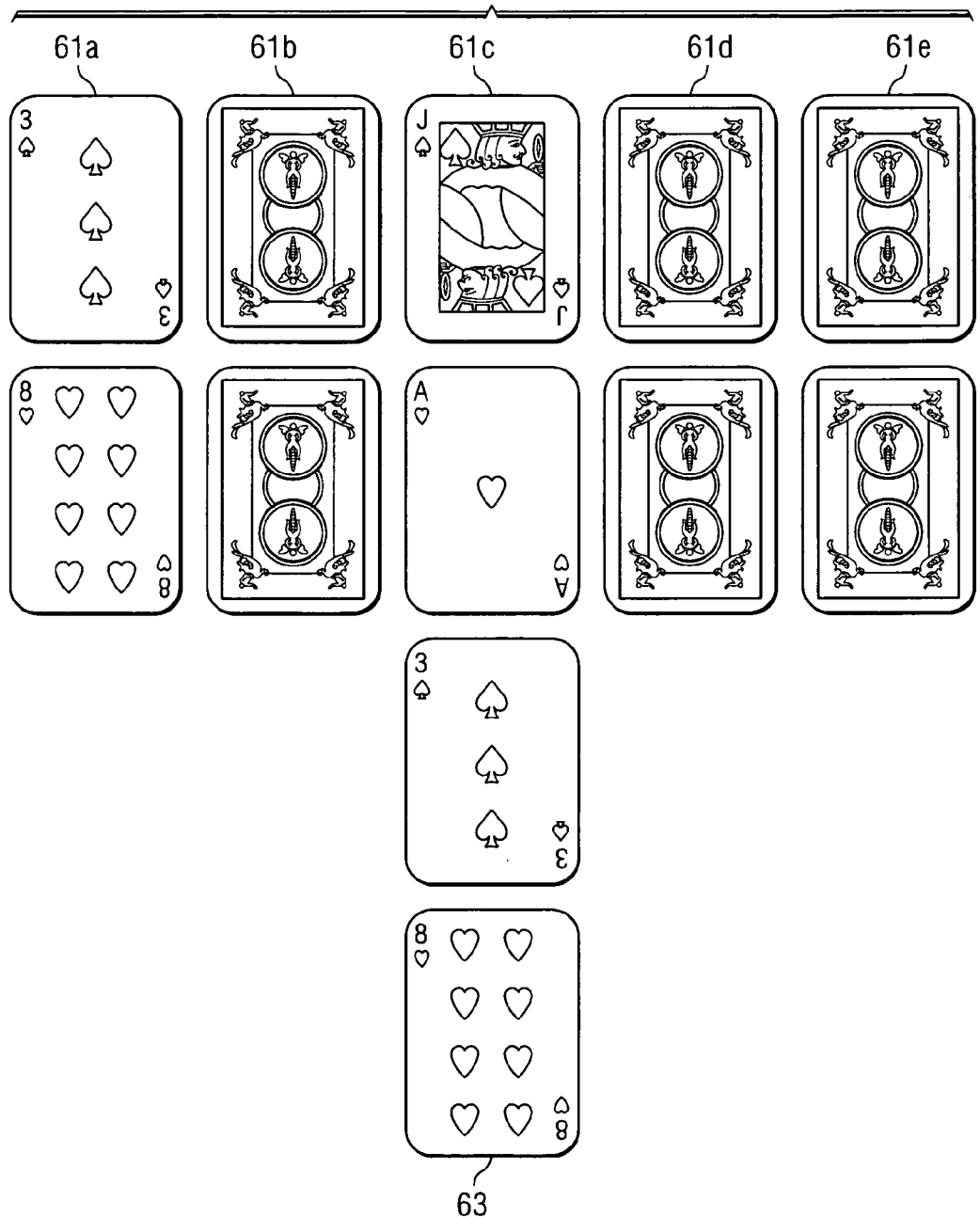

Testing Phase: The test proper is exactly the same format using normal appearing playing cards, though the subject must respond and no arrows appear. The sliding appearance of the hand(s) 30, 31 from the bottom of the computer monitor indicates they should prepare to start responding. In addition, the card pack 33 (FIG. 10) & keyboard 19 disappear briefly and redraw. A single pack of face-down cards 33 then appears centrally concomitantly with a shuffling sound. After a variable period, between 1500–2500 ms, a face-up card 35 (randomly selected) appears on top of the central deck. At the same time, the correct true/false key highlights. These remain as they are until a key (23, 25, 27) is pressed. A reaction time is then recorded, and visual feedback commences (the correct key unhighlights and, if they correctly pressed this key, the card moves to the right turning over to face-down and slides underneath the deck or, if an incorrect key was pressed, turns to the left initially and an error buzzer sounds). This repeats with the ISI varying between 1500–2500 ms always showing a randomly selected card. If a trial takes longer than 5000 ms then the error feedback occurs whether or not the subject responds. The keyboard disappears after 3 correct consecutive trials and will reappear after 3 incorrect consecutive responses. The test ends when 14 correct responses have occurred to either red or black cards, or a total test time of 60 seconds has elapsed.

Figure 7:
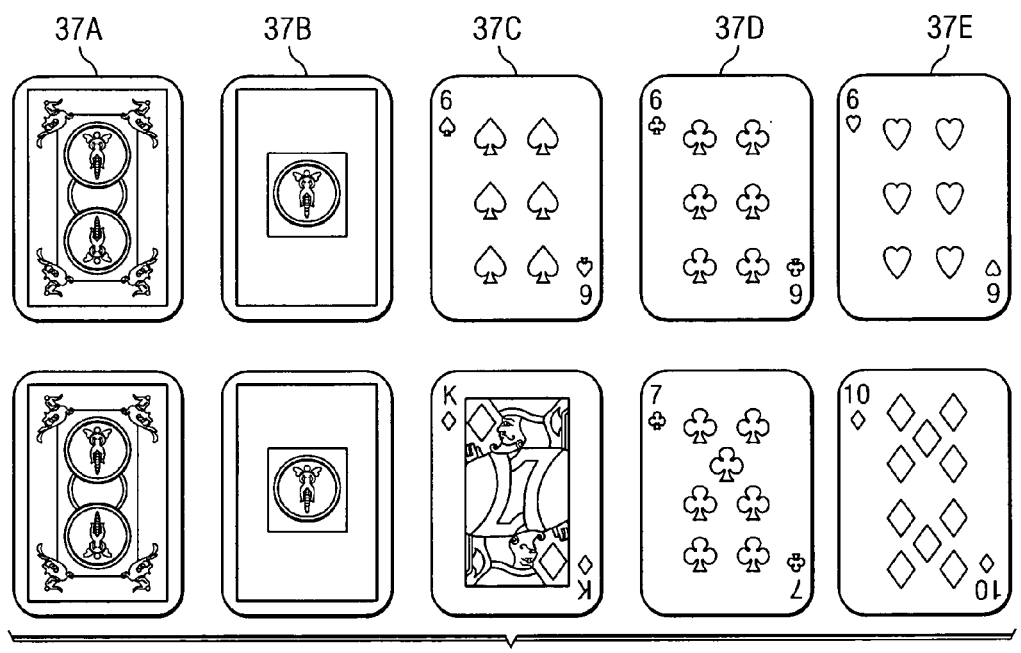
FIG. 7 shows cards used in a congruent test.

Trial Settings:
    Total required successes=7 blacks+7 reds (or total of 14)
    Stimulus Start=1500 ms
    Stimulus Stop time=0 ms
    Feedback duration=200 ms
    Post-ISI random range=0–1000 ms
    Minimum reaction time start=1600 ms
    Maximum time for trial=5000 ms
    4. Congruent Test—See FIG. 7.

Aim: To assess a subject's efficiency in a more complex choice reaction task, here choosing between congruent card suit colours when confronted by two face-up cards placed vertically. Adding this more complex choice component should further increase reaction time by 50–150 ms approximately over the choice reaction time. This allows a regression line to be constructed showing increasing reaction time with increasing stimulus demands.

Simulation Phase: A simulation first shows what the subject is expected to do. They initially see the keyboard (without hands) with the true and false keys outlined in red, and a central pack of cards face-down which then splits sliding another pack of face-down cards below it. Hence, this appearance is similar to the choice reaction time task just completed though differing by an extra pack of face-down cards 37D. At random intervals between 1500–2500 ms two cards appear face-up on their piles and the correct response key highlights (with an additional key pressing sound or click). A yellow shadowed arrow appears from the base of the lowest face-up card pointing to the correct key to indicate it should be pressed as soon as this combination of cards turn face-up. The cards in the simulation are not proper cards, but the same red or black colour filled rectangle cards 37B used in the choice reaction time task. The presentation of these is again randomized during the simulation (ie. whether two congruent or different colour cards) but continues until at least two of each configuration have been presented and then the test proper begins.

Testing Phase: The test proper is exactly the same format using normal appearing playing cards, though the subject must respond and no arrows appear. The sliding appearance of the hand(s) from the bottom of the screen indicates they should prepare to start responding. In addition, the card packs & keyboard disappear briefly and redraw. The dual pack of face-down cards appears again centrally concomitantly with a shuffling sound. After a variable period, between 1500–2500 ms, randomly selected face-up cards 37C, 37D, 37E appear simultaneously on top of each deck. At the same time, the correct true/false key highlights. These remain as they are until a key is pressed. A reaction time is then recorded, and visual feedback commences (the correct key unhighlights and, if they correctly pressed this key, both cards move to the right turning over to face-down and sliding underneath the deck or, if an incorrect key was pressed, turning to the left initially with an error buzzer sounding). This sequence repeats with the ISI varying between 1500–2500 ms always showing randomly selected cards. If the trial takes longer than 5000 ms then the error feedback occurs whether or not they have responded. The keyboard disappears after three correct consecutive trials and will reappear after three (or more) incorrect consecutive responses. The test ends when fourteen correct responses have occurred to either congruent or non-congruent card pairs, or a total test time of sixty seconds.

Figure 8:
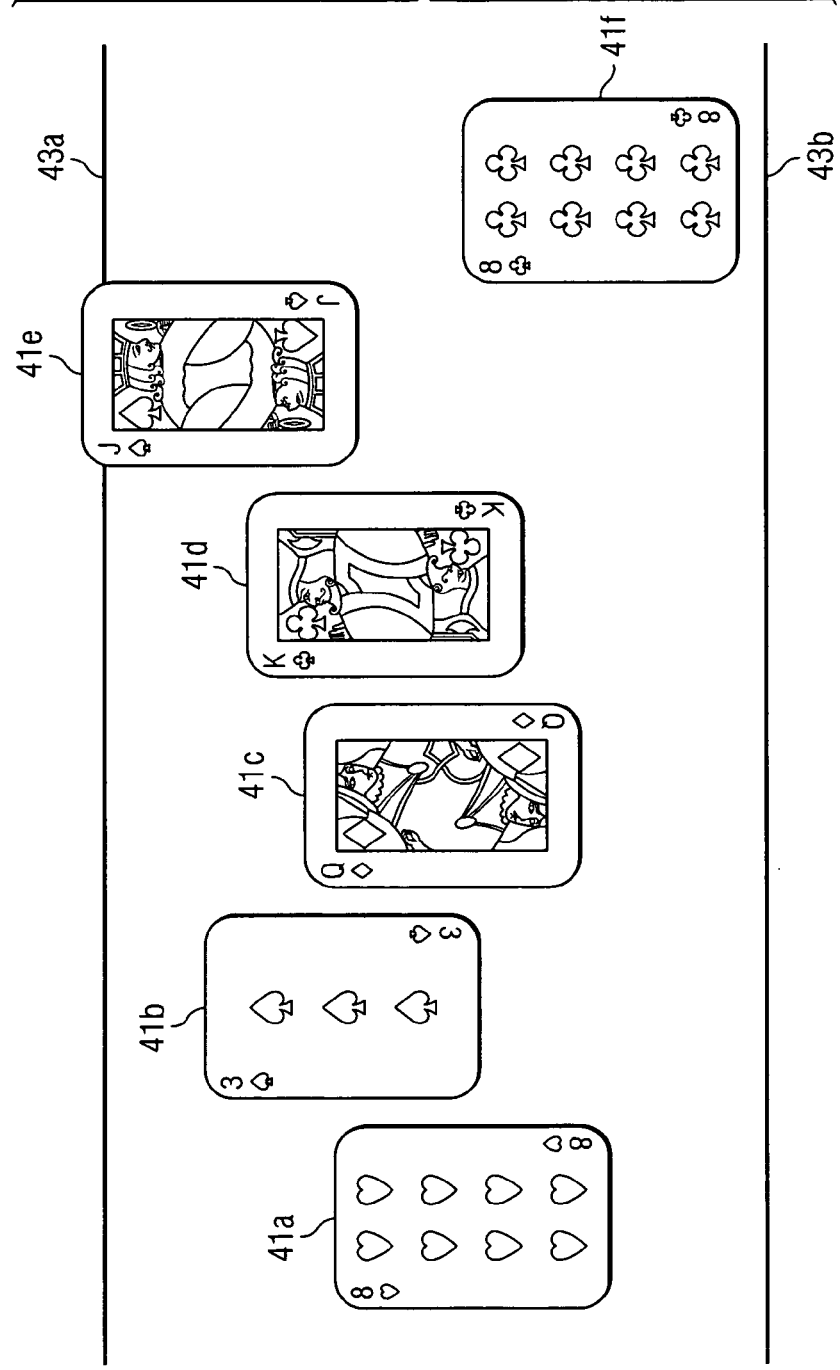
FIG. 8 shows cards used in a continuous monitoring test.
Figure 9A:
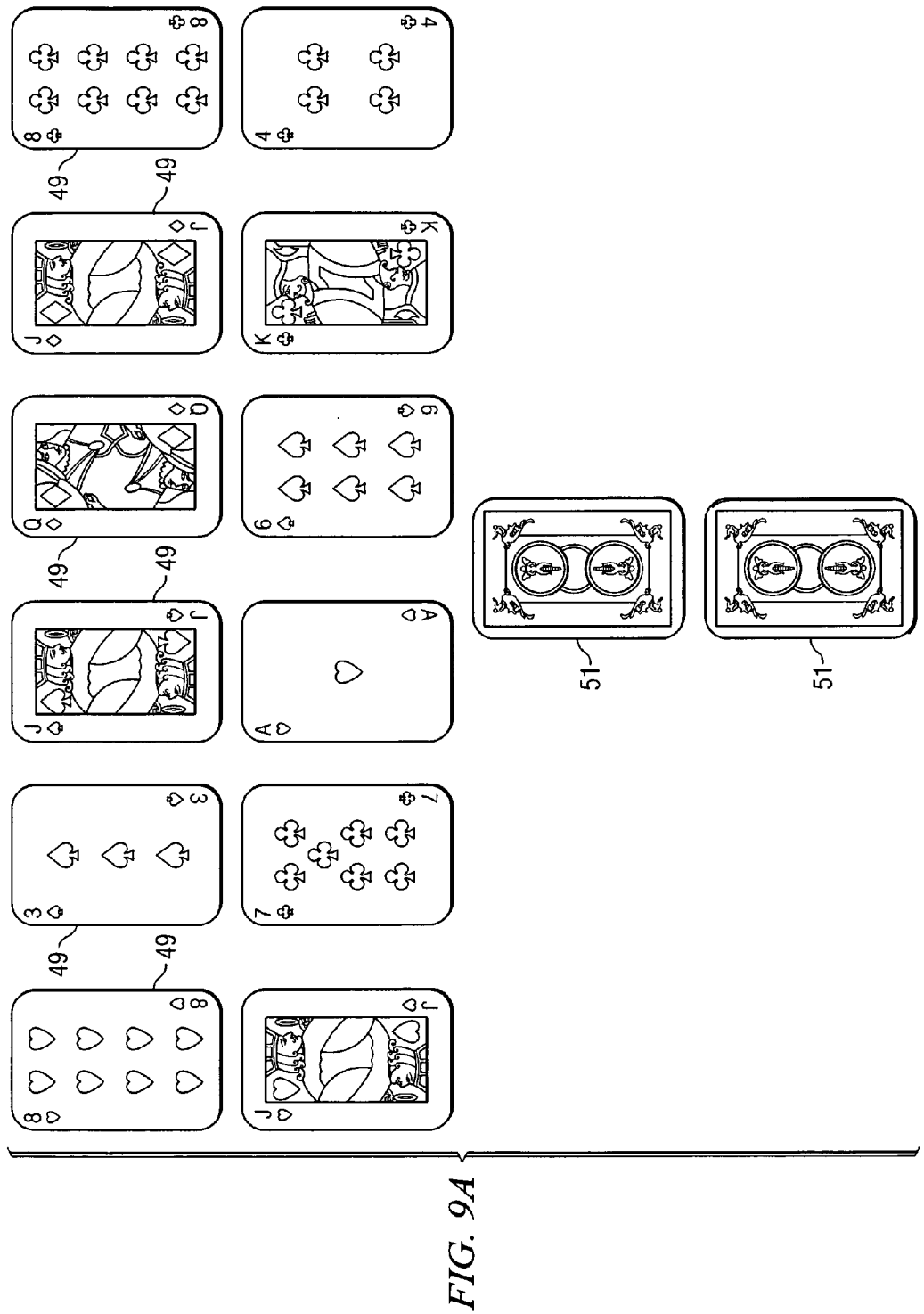
FIGS. 9A and 9B show cards used as a pair card matching test with incidental memory.
Figure 9B:
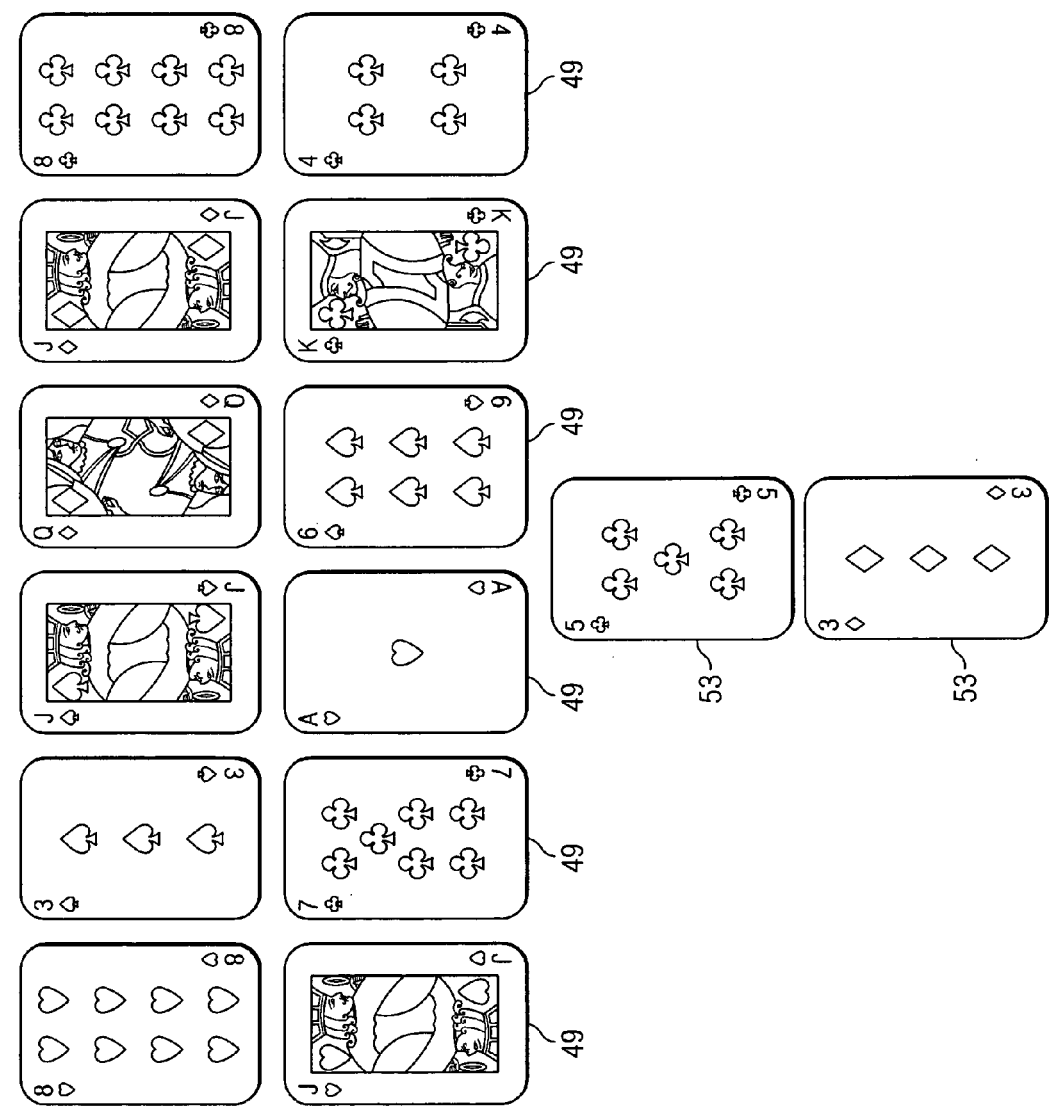

Trial Settings:
    Total required successes=7 congruent+7 non-congruent (or total of 14)
    Stimulus Start=1500 ms
    Stimulus Stop time=0 ms
    Feedback duration=200 ms
    Post-ISI random range=0–1000 ms
    Minimum reaction time start=1600 ms
    Maximum time for trial=5000 ms
    5. Continuous Monitoring Test—See FIG. 8.

Aim: This is the first of three linked tests. It measures vigilance and is a continuous performance task. It trains subjects in an expectant monitoring task which is later combined with another choice decision task in order to test divided attention. The rule they should acquire here is to press the space bar when any card touches a white line. The white lines are horizontally placed equidistantly above and below the original face-down pack's location vertically.

Simulation Phase: A simulation first shows what the subject is expected to do. They initially see the keyboard 19 (without hands) with the space bar key 27 outlined in red, and five vertically centred face-up cards. The horizontal lines 43 are above and below these cards 41. The cards 41 move up or down continuously and seemingly randomly. They can thus move up at any point in time progressively, hover in the same approximate location or move down progressively. It is not possible to predict reliably which way a card 41 will move. All cards are constantly moving and at some point during the simulation a card 41 touches either the upper or lower limiting line. The cards 41 stop and a yellow arrow appears from bottom of the line-touching card to the space bar key which highlights simultaneously. After a few seconds, the demonstration continues and the card which was touching the line becomes centred vertically and the space bar key unhighlights. This continues until at least one card 41 has touched the upper and lower limit (not necessarily the same card). The cards 41 in the simulation are proper cards.

Testing Phase: The test proper is exactly the same format, though the subject must respond and no arrows appear. The sliding appearance of the hand(s) 30, 31 from the bottom of the screen indicates they should prepare to start responding. In addition, the cards 41 & keyboard disappear briefly and redraw. The five face-up cards 41 appear again centred vertically concomitantly with a shuffling sound and begin their jittery pseudo-random movements up and down. After a variable period, one card 41e will touch a line and at the same time, the space bar key 27 highlights. From then onwards this card 41e will travel away from the centre (but no further than a half a vertical card dimension beyond the upper or lower white line) so that it is no longer-equivocal as to whether the line has been crossed. These continue away from the centre or at the maximum allowed limit until the space bar key 27 is pressed. A reaction time is then recorded, and visual feedback commences (the space bar key unhighlights and, if they correctly pressed this key, the errant card or cards re-centre). If an incorrect key is pressed, an error buzzer sounds and the outlier card does not change position. In addition, if the space bar key is pressed when no card 41 is touching or beyond a line 43, the error buzzer also sounds and an anticipatory error is recorded. If the subject does not respond after a card has been beyond a line for over two seconds, then this card jumps back a half card distance towards the centre and moves again outwards. This aims to attract attention to persistently missed cards. The cards 41 move each time with a minimum of six pixels, and variable additional steps of 0–6 pixels. One "favoured" card (randomized to a different card when this favoured card reaches a line) has an additional gain factor (±4 pixels) added to it. If the gain factor is positive this biases movement towards the lower line 43b, and if negative towards the upper line 43a. The keyboard 19 disappears after three correct consecutive trials and will reappear after three (or more) incorrect consecutive responses. The test ends when fourteen correct responses have occurred to either upper or lower migrating cards, or a total test time of 60 seconds.

Trial Settings:
  Total required successes=14
  Stimulus Start =0 ms
  Stimulus Stop time=0 ms
  Feedback duration=0 ms
  Post-ISI random range=0 ms
  Minimum reaction time start=0 ms
  Maximum time for trial=99999999 ms (about 27.8 hours)
  6. One-back Test
  Aims: This is the second of the three tests designed to assess divided attention. This is a working memory task in which the subject must remember the prior card when responding. It is termed a "one-back" test due to the requirement to remember only the last presented card. This is also a training task for the next combined test.

Simulation Phase: A simulation first shows what the subject is expected to do. They initially see the keyboard 19 (without hands 30, 31) with the true 23 and false 25 keys outlined in red, and a single central pack of cards face-down above the keyboard. Hence, this appearance is similar to the choice reaction time task they have already performed. At random intervals between 1500–2500 ms a card appears face-up on the pile and the correct response key highlights. A yellow shadowed arrow appears from the base of the face-up card pointing to the correct key to indicate it should be pressed as soon as this type of card turns face-up. The cards in the simulation are not proper cards however, but have red or black circles—i.e. circles of a single colour instead of the suits, a number (or letter for J, Q, K) at the top left and the correct number of circles. These are meant to indicate the subject should only be concerned with the number of the card. The red or black filled circles indicates that suit is not relevant to the pairing. The simulation items shown include all possible variations for consecutive cards. Hence, if a pair with both red, both black and either red or black comes up and the true key is highlighted, as well as non-sequential pairs (ie. different card face values) with the false key highlighted. This should be sufficient for most subjects to work out the rules for responding, though this is not as easy as the prior tests. The simulation continues until at least one of each of the possible sequences has appeared (and will favour these if they are not present by chance), and then the test proper begins.

Testing Phase: The test proper is exactly the same format using normal appearing playing cards, though the subject must respond and no arrows appear. The sliding appearance of the hand(s) from the bottom of the screen indicates they should prepare to start responding. In addition, the card pack 33 & keyboard 19 disappear briefly and redraw concomitantly with a shuffling sound. After a variable period, between 1500–2500 ms, a face-up card 35 (randomly selected) appears. At the same time, the correct true 23/false 25 key highlights. These remain as they are until a key 23,25,27 is pressed. A reaction time is then recorded, and visual feedback commences (the correct key unhighlights and, if they correctly pressed this key, the card moves to the right turning over to face-down and sliding underneath the deck or, if an incorrect key was pressed, turning to the left initially with an error buzzer sounding). This sequence repeats with the ISI varying between 1500–2500 ms always showing randomly selected cards. If the trial lasts longer than 5000 ms then the error feedback occurs whether or not they have responded. The keyboard disappears after three correct consecutive trials and will reappear after three (or more) incorrect consecutive responses. The test ends when fourteen correct responses have occurred to either sequential paired or non-paired cards, or a total test time of ninety seconds.

Trial Settings:
  Total required successes=14
  Stimulus Start=1500 ms
  Stimulus Stop time=0 ms
  Feedback duration=200 ms
  Post-ISI random range=0–100 ms
  Minimum reaction time start=1600 ms
  Maximum time for trial=5000 ms
  7. Combined Monitoring/One Back Test
  Aims: This is the combination of tests five & six aiming to assess divided attention. This is a difficult task in which errors or prolonged reaction times are likely to be common. The subject must perform the one-back task occurring in the contra card, whilst observing five cards as they jitter between the two white horizontal lines.

Simulation Phase: There is no specific simulation component to this test. The simulation having been provided by the previous two tests. The One-Back task just continues from the previous test with horizontal lines appearing and initiation of the jittering vertical movement of the single central card. After several correct responses are recorded, four other jittering cards appear on either side of the first as in the Monitoring task. They do not change, nor are their denominations important in the test. There is no keyboard at the bottom of the screen for guidance. When the test begins the subject is expected to remember which keys must be used from the previous tests.

Testing Phase: The test proper continues using exactly the same format. As before after a variable period, a card 41 or more will touch a white line and at the same time, the space bar key highlights. From then onwards this card will travel away from the centre (but no further than a half a vertical card dimension beyond the upper or lower white line) so that it is no longer equivocal as to whether the line has been crossed. These continue away from the centre or at the maximum allowed limit until the space bar key is pressed. A reaction time is then recorded as for the monitoring task, and visual feedback commences (if they correctly press the space bar key, the errant card or cards re-centre). If an incorrect key is pressed, which is not relevant to the one-back task, an error buzzer sounds and the outlier card does not change position. In addition, if the space bar key is pressed when no card is touching or beyond a line, the error buzzer also sounds and an anticipatory error is recorded. If the subject does not respond after a card has been beyond a line for over two seconds, then this card jumps back a half card distance towards the centre and moves again outwards. This aims to attract attention to persistently missed cards. The cards move each time with a minimum of six pixels, and variable additional steps of 0–6 pixels. One "favoured" card (randomized to a different card when this favoured card reaches a line) has an additional gain factor (±4 pixels) added to it. If the gain factor is positive, this biases movement towards the lower line, and if negative towards the upper line.

The one-back task executes simultaneously using normal appearing playing cards, though the subject must respond and no arrows appear. This task will seem independent of the monitoring one. After a variable period, between 1500–2500 ms, the central face-down card turns face-up card revealing a randomly selected card. This remains until either the true or false key is pressed. A reaction time is then recorded, and visual feedback commences (if they correctly pressed the true or false key, the card moves to the right turning over to face-down and sliding underneath the deck or, if an incorrect key was pressed, turning to the left initially with an error buzzer sounding). This sequence repeats with the ISI varying between 1500–2500 ms always showing randomly selected cards. If the card remains face-up for longer than 5000 ms then the error feedback occurs whether or not they have responded.

The keyboard may appear after three incorrect consecutive responses. The test ends when fourteen correct responses have occurred to either upper or lower migrating cards, and fourteen correct one-back responses, or a total test time of 90 seconds.

Trial Settings:
    Total required successes=14 one-back and 14 line-crossings
        Stimulus Start=1500 ms
        Stimulus Stop time=0 ms
        Feedback duration=200 ms
        Post-ISI random range=0–1000 ms
        Minimum reaction time start=1600 ms
        Maximum time for trial=5000 ms
        8. Paired Card Matching Test (with Incidental Memory)
        Aims: To assess matching to sample speed and accuracy.
Six pairs of different cards appear above a dual pack of face-down cards. Cards appear face-up on these packs and the subject has to decide whether they are part of the six pair legend or not. After these have been matched multiple times, incidental learning of these pairs is tested. No feedback occurs during this memory testing section. It is expected that subjects with poor retentive memory abilities will do particularly poorly on the incidental memory component.

Simulation Phase: A simulation component first shows what the subject is expected to do. They initially see the keyboard 19 (without hands 30, 31) with the true and false keys outlined in red, and a single central pack of cards face-down above the keyboard. The pack splits in two and the second half slides below the initial pack. Cards then flip and move upwards to form two rows of three card pairs centred horizontally above the face-down packs. At random intervals between 1500–2500 ms two cards appear face-up on the piles and the correct response key 23, 25 highlights. A yellow shadowed arrow appears from the base of the face-up cards pointing to the correct key to indicate it should be pressed as soon as this combination of cards turn face-up. The cards in the simulation are proper cards. The demonstration items show both true and false conditions. Hence, if a pair which is also in the 6-card legend appears, this is regarded as a true condition, and a false condition is where a pair that is not in the key appears. To facilitate learning of the pairs no equivocal pairs—i.e. pairs having one of the two cards of the "true" legend pairs of cards—will ever appear. Visual feedback differs for these conditions. For true pairs, the cards slide quickly to their matching cards. For false conditions, the cards turn face-over and slide underneath the packs. This should allow subjects to work out the rules for responding. They are not shown a simulation of the memory component. The simulation continues until at least two of each of the true and false conditions has appeared (facilitated if chance is taking too long), and then the test proper begins.

Test Phase: The test proper is exactly the same format, though the subject must respond and no arrows appear, and there are now six card pairs 49 (ie. twelve cards in total). The sliding appearance of the hand(s) 30, 31 from the bottom of the screen indicates they should prepare to start responding. In addition, the card packs & keyboard disappear briefly and redraw concomitantly with a shuffling sound. Finally, 6-card pairs 49 are flipped over from the 2 face-down packs to indicate a new and larger set of cards will be used in the legend in the real test. After a variable period, between 1500–2500 ms, two randomly-selected face-up cards appear 53. At the same time, the correct true/false key highlights. These remain as they are until a key is pressed. A reaction time is then recorded, and visual feedback commences as before (the correct key unhighlights and, whether they correctly pressed this key or not, the cards slide upwards to their matching card in the legend, and if the false condition, the cards flip to the right and slide underneath the pack). If they were incorrect in their key response, an error buzzer sounds. They are not forewarned about the memory component, though it is expected that after performing the test several times, they will be aware of the need to commit the legend's pairs to memory. This sequence repeats with the ISI varying between 1500–2500 ms always showing randomly selected card pairs either in the legend or not, until the legend pairs have been displayed twice each, and non-legend pairs at least six times. If a trial lasts longer than 5000 ms then the error feedback occurs whether or not they have responded. The keyboard disappears after three correct consecutive trials and may reappear after three incorrect consecutive responses. When the learning component has completed, the incidental memory component begins. This section finishes if more than 80 seconds has elapsed and moves onto the memory testing component.

The legend disappears and card pairs continue to turn over (Incidental learning test). No error feedback is given and cards always flip over to the right and slide under their piles regardless of the key pressed. No error buzzer sounds. If the subject takes longer than 5000 ms then the error feedback occurs. About 30 successful responses are required to complete this test. Card pairs flip over to face-up at 1500–2500 ms intervals until all legend card pairs have been shown at least once and a similar number of non-legend card pairs has appeared, or a total of 150 seconds for both components has elapsed.

Trial Settings:
  Total required successes=12 legend pairs, 6 foils, and then 6 of each in memory component
  Stimulus Start=1500 ms
  Stimulus Stop time=0 ms
  Feedback duration=200 ms
  Post-ISI random range=0–1000 ms
  Minimum reaction time start=1600 ms
  Maximum time for trial=5000 ms
  9. Associate Learning Test Aims: This final test allows assessment of both learning & retentive memory, with a matching ability control test included. It resembles the paired-card matching test (number 8) in layout, except that all but one pair in the legend is face-down. Thus the subject must remember the hidden cards in the pairs. The face-up pair can be matched directly by comparison without the need to remember it. This is the control pair, since patients with primary memory disorders should be able to match even though they cannot recall the hidden cards. Some subjects with feigned memory loss might be expected to have trouble with both hidden and displayed pair matching (beyond a chance level). This is a hard test which should be a good discriminator of memory & concentration ability. In addition, it is presented as the last test to maximize the detrimental effects of fatigue or poor concentration. It is also expected that subjects will not recall all four pairs correctly on the first presentation, but that a learning curve will occur such that errors are corrected with subsequent feedback.

Simulation: A simulation first shows what the subject is expected to do. It is very similar to the paired-cards matching test just completed. They initially see the keyboard 19 (without hands) with the true and false keys outlined in red, and a single central pack of cards face-down above the keyboard 19. The pack splits in two and the second half slides below the initial pack. At random intervals between 1500–2500 ms, two cards appear face-up on the piles and the correct response key highlights. A yellow shadowed arrow appears from the base of the face-up cards pointing to the correct key to indicate it should be pressed as soon as this combination of cards turn face-up. The cards in the demonstration are proper cards. The first condition is a false condition, since no card pairs have been seen before. The initial part of this demonstration displays each of the three pairs to be remembered twice in succession. The first time, when the pair is new, the false key should be pressed (since, to reiterate, the pair has not been seen before). Thereafter, if that pair appears again, the true key should be pressed. When the response has occurred, in the initial learning phase, the pair of cards slides upwards to form a grid above the dual pack of cards. These will build into a two row by three column grid. For the demonstration, the two outer pairs will be mainly face-down whilst the central pair is face-up throughout. There are three pairs in the demonstration task. Once a pair of cards has turned over, and the arrows removed, the correct key unhighlights and visual feedback occurs. If the card pair is part of the set to be remembered, the matching card pair in the legend flip to face-up, and the stimulus cards slide to their matching grid position (from left to right) so the subject can see they are the same as the new pair, wait about 0.5 seconds, and then flip over in-situ so they are face-down. The central pair in the legend, however, never turns face-down but the other similar feedback occurs.

Once all the simulation card pairs (6 cards) have appeared twice, random presentation of pairs occurs such that either a legend's pair or a non-legend's pair appears. If the pair matches one in the legend, the true key highlights and is pointed to by an arrow. Once this vanishes, the cards of the pair slide to their correct positions (with first flipping of the legend's face-down cards). If a pair appears that does not exactly match any of the legend's pairs, then the false key is highlighted and the cards of the pair flip over to the right of their packs and then slide underneath their decks. Both unequivocal and equivocal foils (ie. with none or one only of the cards of a true legend pair respectively) can occur so that the subject must truly recall both cards of the pair to be completely accurate. This simulation should allow subjects to work out the rules for responding, though they will realize this is a difficult test. The simulation continues until at least two of each of the true and false conditions has appeared after all legend cards have been laid out, and then the test proper begins.

Testing Phase: The test proper is exactly the same format, though the subject must respond and no arrows appear, and there will now be 5 card pairs (ie. 4 face-down card pairs 61a, 61b, 61c, 61d, 61e with a centrally placed face-up pair 61c, FIGS. 10A and 10B). The sliding appearance of the hand(s) from the bottom of the screen indicates they should prepare to start responding. In addition, the card packs & keyboard 19 disappear briefly and redraw concomitantly with a shuffling sound, and the legend disappears completely. As in the demonstration, the legend's card pairs are incrementally built, as part of the learning process (called "drilling") by showing a new pair 61a, then moving it into its grid position after a response key then repeating the same pair 61a and sliding it over the prior grid-situated pair. A card pair 61 appears after a variable period between 1500–2500 ms. Card pairs are selected randomly so that no cards are repeated and no pair 61 is the same from test to test. At the same time as the pair appears, the correct true/false key highlights. These remain as they are until a key is pressed. A reaction time is then recorded, and visual feedback commences as discussed in the simulation except that the grid's corresponding face-down pairs are not flipped over. The new card pair slides directly to the appropriate pile, and then flips to face-down. If the pair is not part of the legend, they flip over to the right and then slide underneath their respective packs. If the response key was incorrect, an error buzzer sounds. This sequence repeats with the ISI varying between 1500–2500 ms always showing randomly selected card pairs either in the legend or not, until the legend pairs have been displayed five times each, and non-legend pairs an equal number of times. If an individual trial lasts longer than 5000 ms then the error feedback occurs whether or not they have responded. The keyboard disappears after three correct consecutive trials and may reappear after three incorrect consecutive responses. The test also ends if more than four minutes elapses.

Trial Settings:
  Total required successes=20 legend pairs, 20 non-legend pairs
    Stimulus Start=1500 ms
    Stimulus Stop time=0 ms
    Feedback duration=200 ms
    Post-ISI random range=0–1000 ms
    Minimum reaction time start=1600 ms
    Maximum time for trial=5000 ms The test can be cancelled at any time using predetermined commands. The subject is warned that their data will be lost if the cancel and they are given an opportunity to change their minds.

Once the test is completed, the subject may then be asked whether they wish to e-mail the tests to a central server for analysis. The act of sending constitutes acceptance of billing for that test. If they are not connected directly to an active Internet connection at the time, they may wish to defer mailing the test results. If they, or their supervisor, do not wish to keep the test results, they can cancel the test. If they defer or mail the test data for analysis, the supervisor details and test data are encrypted in accordance with a suitable encryption technique and stored in the subject data file. In addition, initial analysis occurs to create the abstracted test parameters required for comparison to normative data and serial performances, and this is stored encrypted as another block in the subject file. If they cancel the process, no supervisor, test data or analysis results will be stored in their file.

In an alternative, the test is carried out "on-line" in real-time and the results are gathered automatically by the host computer.

Normative data will be collected before final algorithms to create results parameters are finalized. Simple descriptive statistics will compute mean and variability measures about the mean for all tests giving an indication of psychomotor speed and consistency. In addition, some test data will be grouped to allow across test comparisons, eg. simple reaction time, choice reaction time and congruent reaction time test data allows a regression line, gradient and intercept to be calculated. Comparisons of monitoring and one-back tests with performance on the combined monitoring task will be made (creating a novel parameter to measure decrement in performance due to the additional cognitive "load"). Errors will be analyzed to give measures of efficiency and accuracy by constructing parameters for (but not limited to) impulsivity, perseveration, spatial (peripheral, right or left) error scores, adaptability (initial eradication of errors), instability (return of errors once success criteria are reached), and memory acquisition.

Combinations of these base parameters will then be tested in patient populations to determine whether they are sensitive to brain dysfunction, and more importantly what profiles of score impairments are associated with particular causes of brain dysfunction (depression, anxiety, psychosis, mild cognitive impairment, Alzheimer's disease, frontotemporal dementia and dysexecutive syndromes consequent to head injury, alcohol, post-traumatic stress disorder, etc). In addition, provocative testing will be performed using normal subjects to model sleep deprivation and fatigue, stress, alcohol, THC and benzodiazepine induced impairment, as well as simulated disease or provocative states. These experiments will determine whether combinations of test parameter ranges are sensitive to these perturbations as well as specific to individual ailments (or limited numbers of these) to aid predictive differential diagnosis.

The algorithm underlying each test trial is a process which is highly flexible. All tests use the same algorithm which can satisfy widely varying stimulus presentation & test requirements. This section describes the trial model and its components (FIG. 11).

Figure 11:
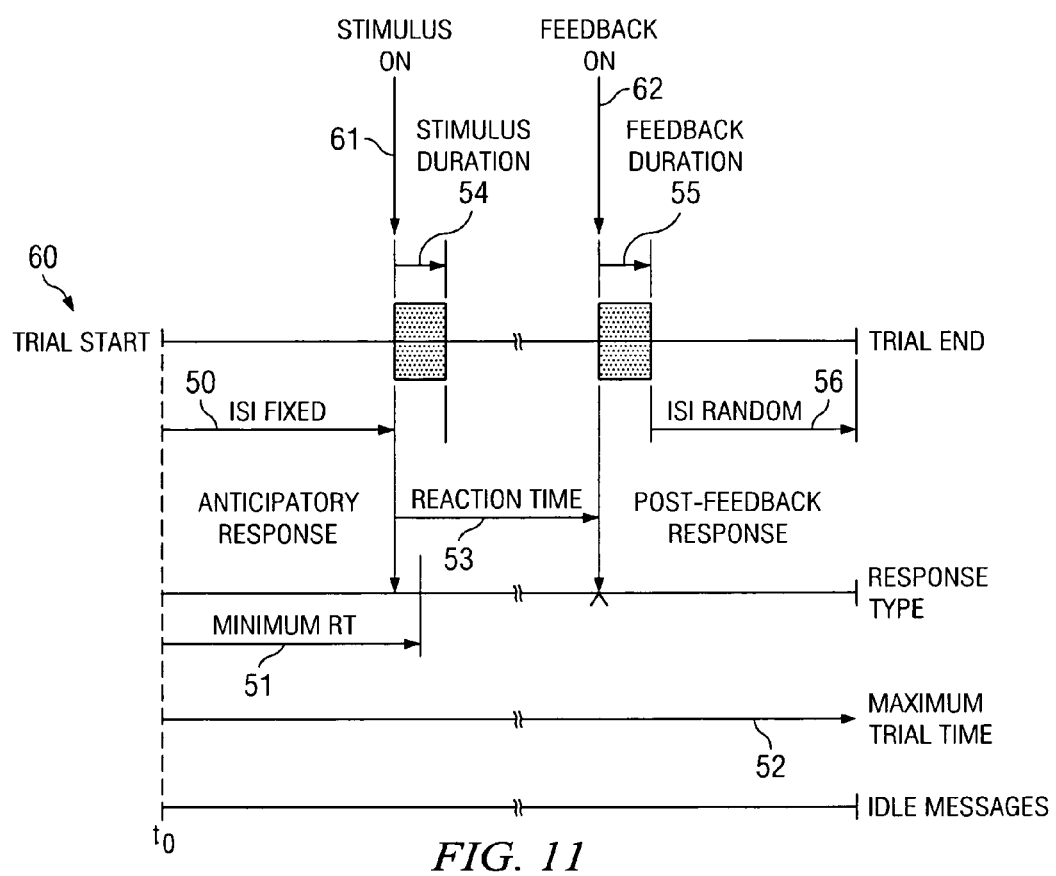
FIG. 11 depicts a trial model and its components.

Each test consists of multiple trials each of which is structured as shown in FIG. 11. The trial has component parts which are active at different stages in the trial timeline. The trial settings record controls exactly what these are.

The trial engine checks boolean flags to determine which part of the timeline has been reached. When a timed interval or specific landmark is reached a corresponding function is called so the test can determine the implementation details (including to ignore it). Idle messages are sent frequently throughout the trial period so updates can occur or complete functionality can be implemented from the idle function.

The trial time intervals measured from the trial start 60 (designated $t_0$ in FIG. 11) are the:
  fixed inter-stimulus interval (ISI fixed 50) which is the time from $t_0$ 60 to stimulus start;
  minimum reaction time (Minimum RT 51) which is the minimum time to record a valid reaction time; any responses detected prior to this time are designated Anticipatory responses;
  maximum trial duration (Max. trial time 52) from $t_0$ 60 to trial end (by definition).
Additional time intervals during the trial are the:
  reaction time (Reaction time 53) measured from stimulus onset 61 to response detected (arrowhead) as long as the max. trial time has not expired;
  stimulus duration 54 from stimulus onset 61 to stimulus end;
  feedback duration 55 from feedback onset 62 to feedback end;
  random inter-stimulus interval (ISI random 56) measured from the end of feedback to trial end; this is usually determined at run time from a given maximum (eg 1000 ms such that any time from 0–1000 ms can be used).

Responses can occur at any time in the trial. If they occur prior to the Minimum RT time they are designated as Anticipatory responses, if after stimulus onset but prior to Max. trial time a valid Reaction time is recorded, and if after feedback has commenced are designated Post-feedback responses. Multiple anticipatory and post-feedback responses can be measured but only one reaction time can be recorded.

The time from stimulus onset to feedback onset is not fixed since it is dependent upon when and whether or not a response is detected. The total duration of the trial is guaranteed to be no more than the Max. trial time, but can be as short as the sum of the Minimum RT, Feedback duration and ISI random intervals. Any of the intervals can be zero, though if all are zero then the trial will occur so quickly it will not effectively execute. However, if all intervals but the Max. trial time are zero, the trial will effectively remain in the Post-feedback response segment. Any responses detected during this time will be reported as Post-feedback responses and can be handled by the subtest in any way appropriate.

The trial also monitors for cancellation of the test either by certain key combinations (customizable by the subtest) or expiration of the total duration of the test.

It will be apparent to a person skilled in the art that various modifications may be made to the testing method and apparatus without departing from the scope and spirit of the invention disclosed herein.

The invention claimed is:

1. A psychological testing method for testing a subject, including:
   performing said method by means of a test presented by means of a testing means having output means and input means; and
   instructing said subject by displaying a test simulation of said test by means of said output means;
   wherein said subject can learn how to perform said test from said simulation, which includes displaying the correct use of the input means to perform said test, and said test includes randomly varying a time at which a visual stimuli is displayed.

2. A psychological testing method as claimed in claim 1, including repeating said simulation a plurality of times.

3. A psychological testing method as claimed in claim 1, wherein said method is performed by means of a plurality of tests, and instructing said subject includes displaying a test simulation of each of said plurality of tests, wherein said subject can learn how to perform each of said tests.

4. A psychological testing method as claimed in claim 1, wherein said subject performing said test by using said input means after said subject is instructed.

5. A psychological testing method as claimed in claim 1, wherein said method includes alternating between said subject being instructed and said subject performing a test.

6. A psychological testing method as claimed in claim 1, wherein said method includes terminating said instructing of said subject and commencing assessing said subject when said subject is able to satisfy a criterion of comprehension of said test.

7. A psychological testing method as claimed in claim 6, wherein said criterion is successful performance of three consecutive trial tests.

8. A psychological testing method as claimed in claim 1, wherein said testing means is a computer programmed to carry out said method.

9. A psychological testing method as claimed in claim 1, wherein said test includes displaying said visual stimuli.

10. A psychological testing method as claimed in claim 1, further including measuring a response time of said subject.

11. A psychological testing method as claimed in claim 10, further including disregarding a response with less than a predetermined minimum response time.

12. A psychological testing method as claimed in claim 9, wherein said visual stimuli are substantially a cultural stimuli.

13. A psychological testing method as claimed in claim 12, wherein said visual stimuli comprise representations of playing card, dominoes, or playing counters.

14. A psychological testing method as claimed in claim 1, further including obtaining a measure of correct and incorrect responses made by said subject.

15. A method of monitoring the performance of a subject, including
   obtaining a reference test result by a subject performing the testing method of claim 1 repeatedly until said subject is satisfied that they have performed said testing method at a near optimum level and using the result of the test performed at a near-optimum level as a reference test result;
   obtaining a comparison test result by a subject performing said testing method repeatedly at a time at which the subject's performance is to be monitored until said subject is satisfied that they have performed the testing method at a near optimum level, and using the result of the test performed at a near optimum level, and using the result of the test performed at a near optimum level as a comparison test result; and
   comparing said comparison test result with said reference test result to thereby monitor the performance of the subject.

16. A method as claimed in claim 15, further including obtaining a number of comparison test results and using said comparison test results to monitor said subject's performance.

17. Psychological testing apparatus for testing a subject, said apparatus including testing means having output means and input means, said testing means testing said subject by presenting a test to said subject, said apparatus instructing said subject by displaying a test simulation of said test on said output means, which includes displaying the correct use of the input means to perform said test, wherein said subject can learn how to perform said test by means of said apparatus from said simulation and said testing means randomly varies a time at which a visual stimuli is displayed.

18. Psychological testing apparatus as claimed in claim 17, wherein said testing means is a computer programmed to present said test to said subject.

19. Psychological testing apparatus as claimed in claim 18, wherein said computer includes a host computer and a client computer connected by a communication network.

20. Psychological testing apparatus as claimed in claim 19, further including a memory associated with said host computer for storing results of said test.

21. Psychological testing apparatus as claimed in claim 19, wherein said communication network is the internet.

22. Psychological testing apparatus as claimed in claim 18, wherein said output means is a display means and more preferably a computer monitor, and said input means includes at least one of is a keyboard or a mouse.

23. Psychological testing apparatus as claimed in claim 17, wherein said testing means repeats said simulation a plurality of times.

24. Psychological testing apparatus as claimed in claim 17 wherein there are a plurality of tests and said testing means displays a test simulation for each said test.

25. Psychological testing apparatus as claimed in claim 17, wherein said testing means is configured to terminate instructing said subject and commence assessment of said subject when said subject is able to satisfy a criterion of comprehension of said test.

26. Psychological testing apparatus as claimed in claim 25, wherein said criterion is successful performance of three consecutive trial tests.

27. Psychological testing apparatus as claimed in claim 17 wherein said testing means presents said visual stimuli.

28. Psychological testing apparatus as claimed in claim 17, wherein said testing means measures the response time of said subject.

29. Psychological testing apparatus as claimed in claim 28, wherein said testing means disregards a response with less than a predetermined in a response time.

30. Psychological testing apparatus as claimed in claim 28, wherein said tests are configured such that any change in response times provides a measure of fatigue of said subject.

31. Psychological testing apparatus as claimed in claim 17 wherein said testing means measure correct and incorrect responses made by said subject.

32. A psychological testing apparatus as claimed in claim 27, wherein said testing means presents substantially a cultural stimuli to said subject.

33. Psychological testing apparatus as claimed in claim 32, wherein said cultural stimuli comprises representations of playing cards, dominoes, or playing counters.

34. Apparatus for monitoring the performance of a subject using the psychological testing apparatus of claim 17, wherein said apparatus obtains a reference test result by allowing a subject to perform the test repeatedly until said subject provides an input via said input means which indicates that the subject is satisfied that they have performed said testing method at a near optimum level, wherein said apparatus includes a storage means for storing said result of the test performed at a near optimum level as a reference test result for said subject;

said apparatus obtaining a comparison test result by allowing a subject to perform said test repeatedly at a time at which the subject's performance is to be monitored until said subject provides an input via said input means which indicates that said subject is satisfied that they have performed the testing method at a near optimum level, said apparatus retrieving the stored reference test result and comparing said comparison test result with said reference test result to thereby monitor the performance of the subject.

35. Use of the method of claim 15 to monitor decline in performance resulting from progression of a clinical condition.

36. Use of the method of claim 15 to monitor changes in performance resulting from therapeutic intervention following obtainment of a reference test result.

37. A method as claimed in claim 15 in which decline in performance resulting from progression of a clinical condition is monitored.

38. A method as claimed in claim 15 in which changes in performance resulting from therapeutic intervention are monitored.

* * * * *